United States Patent [19]

Buell

[11] 4,217,078
[45] Aug. 12, 1980

[54] APPARATUS FOR FORMING A CONTINUOUS REINFORCED FIBROUS WEB

[75] Inventor: Kenneth B. Buell, Wyoming, Ohio

[73] Assignee: The Procter & Gamble Company, Cincinnati, Ohio

[21] Appl. No.: 960,883

[22] Filed: Nov. 15, 1978

Related U.S. Application Data

[62] Division of Ser. No. 810,559, Jun. 27, 1977, Pat. No. 4,141,772.

[51] Int. Cl.$^2$ ............................................. B29B 5/00
[52] U.S. Cl. .................................. 425/81.1; 425/83.1; 425/130
[58] Field of Search ...................... 425/130, 81.1, 83.1

[56] References Cited

U.S. PATENT DOCUMENTS

| | | | |
|---|---|---|---|
| 3,501,558 | 3/1970 | Munters | 264/113 |
| 3,952,745 | 4/1976 | Duncan | 128/287 |
| 3,995,980 | 12/1976 | Van Smith | 264/113 |

Primary Examiner—Donald J. Arnold
Assistant Examiner—James R. Hall
Attorney, Agent, or Firm—E. Kelly Linman; John V. Gorman; Richard C. Witte

[57] ABSTRACT

A continuous in-line method for forming an airlaid fibrous fluff web adjacent the uppermost and lowermost surfaces of a substantially planar internal reinforcing ply having substantially the same width as said fibrous web, said ply being substantially impervious to the passage of fibers from one surface thereof to the other, in a continuous fiber deposition zone is disclosed. In a preferred embodiment, a unique ply folding board is employed to permit continuous formation of an airfelt web having a reinforcing ply comprised of wet strength tissue paper located approximately mid-way between its uppermost and lowermost surfaces. Two adjacent vacuum chambers are preferably employed in the continuous forming zone to compensate for the increased airflow restriction encountered when forming the uppermost fibrous web portion over the reinforcing ply and the lowermost fibrous web portion. In a particularly preferred embodiment, the position of the internal reinforcing ply relative to the uppermost and lowermost surfaces of the resultant airfelt web may be adjusted by advancing or retarding the position of the folding board within the fiber deposition zone.

9 Claims, 8 Drawing Figures

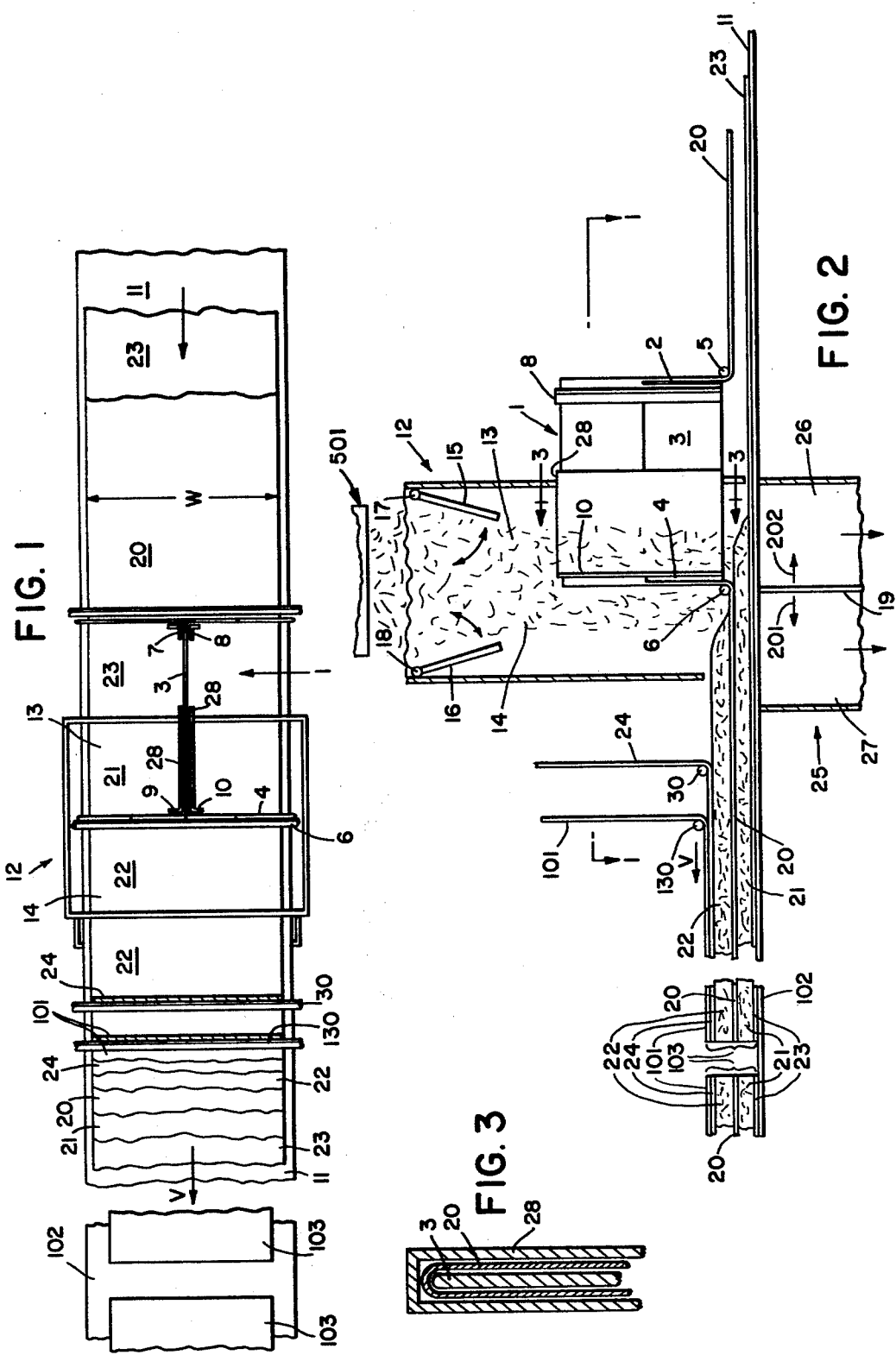

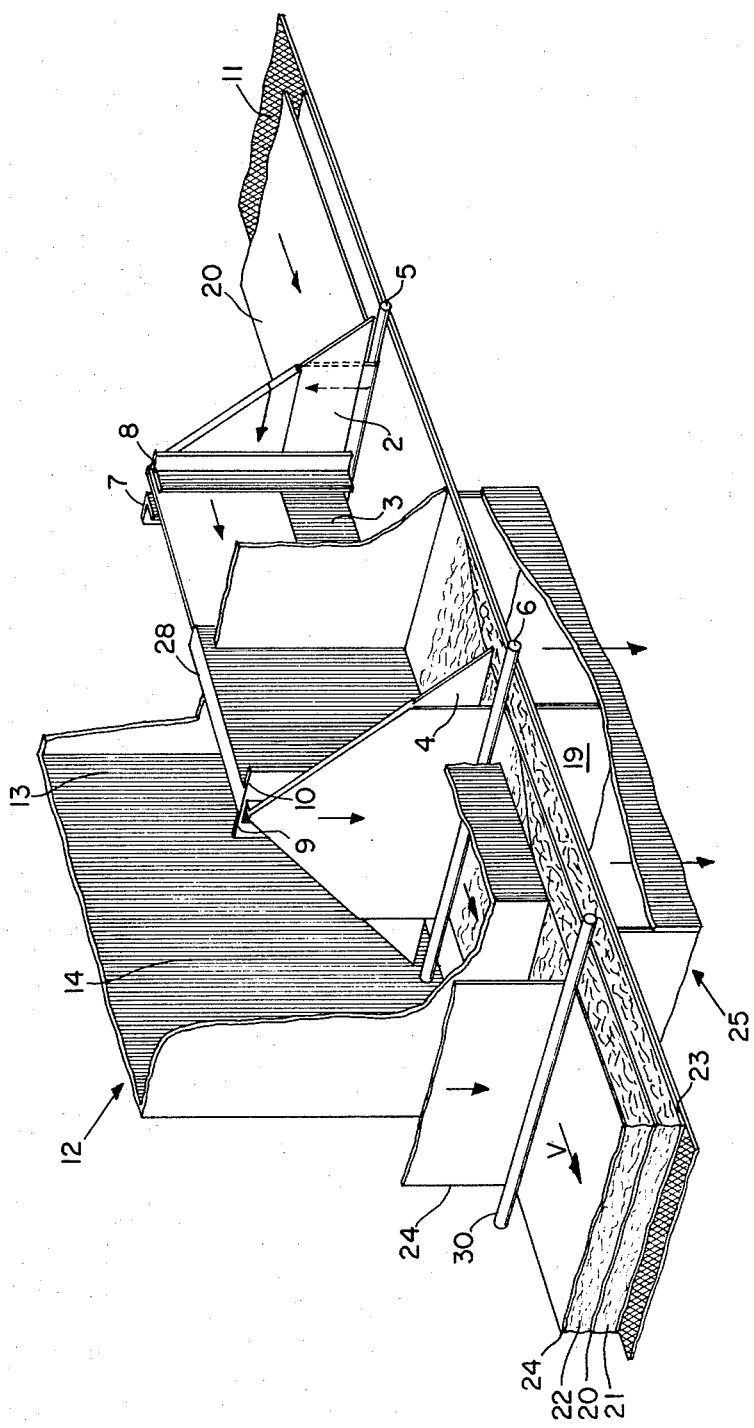

APPARATUS FOR FORMING A CONTINUOUS REINFORCED FIBROUS WEB

This is a division of application Ser. No. 810,559, filed June 27, 1977, now U.S. Pat. No. 4,141,772.

BACKGROUND OF THE INVENTION

Absorbent fibrous structures comprised of low strength absorbent materials such as airlaid wood pulp fibers are well known in the disposable absorbent bandage art. In certain of these prior art fibrous pad structures it has been found desirable to employ one or more internally located plies of tissue paper or other web materials which are substantially impervious to the passage of fibers to act, for example, as a reinforcing agent, as a fluid baffle to distribute absorbed fluids within the absorbent fluff structure, as a partitioning agent or the like. Addition of such internal plies which have a width substantially equal to that of the absorbent fibrous webs located on the uppermost and lowermost surfaces thereof has typically been provided by utilizing a multiplicity of discrete forming zones with a separate fiber supply source for each zone. However, the multiple forming zone approach typically employed by such prior art systems requires considerable converting line space and involves a duplication of disintegrating and air laying equipment for each absorbent fibrous layer employed in the resulting structure. Futhermore, altering the position of the internal ply relative to the uppermost and lowermost surfaces of the finished absorbent pad typically requires a complex adjustment procedure for each fiber deposition zone in the system.

Accordingly, it is an object of the present invention to provide apparatus for forming an airlaid fibrous fluff web adjacent the uppermost and lowermost surfaces of a substantially planar, fiber-impervious internal reinforcing ply having substantially the same width as said fibrous web in a continuous fiber deposition zone.

It is another object of the present invention to provide apparatus for easily altering the position of the internal reinforcing ply relative to the uppermost and lowermost surfaces of the absorbent web in question.

It is yet another object of the present invention to provide apparatus for forming an airlaid fibrous fluff web adjacent the uppermost and lowermost surfaces of a substantially planar, fiber-impervious, internal reinforcing ply having substantially the same width as said fibrous web in a continuous fiber deposition zone having an overall length no greater than that required to form an identical absorbent web of comparable basis weight without said internal reinforcing ply.

SUMMARY OF THE INVENTION

In simplest terms, the present invention accomplishes the aforementioned objectives by carrying out the steps of:
(a) continuously feeding a substantially planar reinforcing ply in a first direction in a first plane;
(b) introducing said moving reinforcing ply to a fiber deposition zone while said ply is oriented so that the direction of fiber flow is substantially parallel to the width of said ply to form the portion of said airlaid fibrous fluff web adjacent the lowermost surface of said reinforcing ply;
(c) guiding said moving reinforcing ply into contact with a first equal length leg portion of the trailing surface of a first planar member exhibiting the shape of an isosceles right triangle, said right triangle having the second of its equal length legs oriented perpendicular to said first direction of travel of said moving ply;
(d) wrapping said moving reinforcing ply about opposite surfaces of said planar member exhibiting the shape of an isosceles right triangle by passing said ply about the hypotenuse thereof;
(e) restoring said moving reinforcing ply to said first direction of travel by passing said moving ply about the second of said equal length legs, thereby causing said ply to assume a planar condition in a second plane perpendicular to said first plane;
(f) exposing the uppermost surface of said moving reinforcing ply to said fiber deposition zone while in a planar condition to form the portion of said airlaid fibrous fluff web adjacent the uppermost surface of said reinforcing ply; and
(g) removing said reinforcing ply from said fiber deposition zone.

In a particularly preferred embodiment, said planar member exhibiting the shape of an isoceles right triangle may be advanced or retarded in the machine direction within the fiber deposition chamber to alter the final position of the reinforcing ply relative to the uppermost and lowermost surfaces of the resultant absorbent fibrous pad.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in connection with the accompanying drawings in which:

FIG. 1 is a simplified cross-sectional illustration of a pad forming mechanism employing a preferred embodiment of the present invention taken along Section Line 1—1 in FIG. 2;

FIG. 2 is a side elevation view of the pad forming mechanism illustrated in cross-section in FIG. 1 with the walls of the fiber deposition chute and the vacuum chamber removed at a point corresponding to the center of the reinforcing ply;

FIG. 3 is an enlarged cross-sectional illustration taken along Section line 3—3 in FIG. 2;

FIG. 4 is a simplified perspective view of the pad forming mechanism illustrated in FIGS. 1-3;

DETAILED DESCRIPTION OF THE INVENTION

Figure 5:
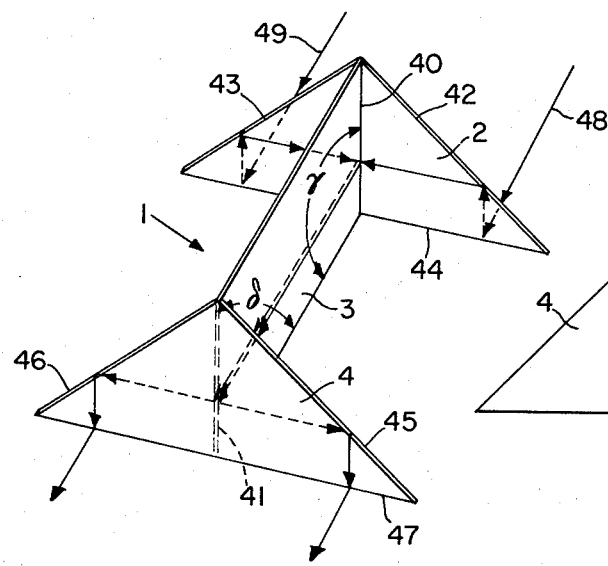
FIG. 5 is a simplified schematic illustration of the folding board portion of the mechanism utilized in a preferred embodiment of the present invention.

FIG. 1 is a plan view of a preferred embodiment of the present invention wherein a wet strength tissue paper reinforcing ply 20 is incorporated intermediate the uppermost and lowermost surfaces of an absorbent pad for a disposable absorbent article to improve its in-use integrity. As can be seen more clearly from FIG. 2, the wet strength tissue paper reinforcing ply 20 is directed about a folding board 1 prior to entry of the reinforcing ply into a fiber deposition chute 12 wherein a lowermost layer of absorbent airfelt 21 is formed beneath the surface of the reinforcing ply 20 and an uppermost layer of airfelt 22 is formed adjacent its uppermost surface. In a particularly preferred embodiment of the present invention, a ply of wet strength tissue paper 23 is employed adjacent the lowermost surface of the layer of airfelt 21, and an uppermost ply of wet strength tissue paper 24 is employed adjacent the uppermost surface of the layer of airfelt 22.

In the embodiment illustrated in FIGS. 1 and 2 the folding board 1 comprises a pair of identical planar members 2, 4 exhibiting the shape of an isosceles triangle and having an included angle of approximately 90° at their respective apexes, said planar members being connected to one another at their altitudes by means of a vertical planar member 3. A reinforcing ply 20, comprised of wet strength tissue paper having a width W substantially equal to that of the airfelt layers 21, 22 is preferably fed in the same direction and at the same velocity V as the foraminous supporting surface 11. The reinforcing ply 20 is caused to alter its path of travel from a horizontal direction to a vertical direction by virtue of being wrapped about direction changing roller 5 located near the base of the isosceles right triangle embodied in planar member 2 forming a portion of the folding board 1. While the center of the moving reinforcing ply 20 is caused to coincide with the altitude of the isosceles right triangle embodied in planar member 2 in the illustrated embodiment, the lateral edge portions of the ply are caused to remain in contact with both the leading and trailing surfaces of the triangle embodied in said planar member by virtue of angular guides 7, 8 located adjacent the interior corners formed between vertical planar member 3 and the triangular planar member 2. When the reinforcing ply 20 is forced to resume its original direction of travel about the apex of the isoceles right triangle embodied in planar member 2, the angular guide members 7, 8 force the reinforcing ply 20 to assume an inverted U-shape as illustrated in the cross-section of FIG. 3. While the vertical planar member 3 does conveniently serve to maintain triangular planar members 2, 4 in longitudinal alignment with one another, its presence is not essential to guide the inverted U-shaped reinforcing ply 20 intermediate the triangular planar members 2, 4. The inverted U-shaped shroud 28 which connects angles 9, 10 to one another serves to prevent fibers within the deposition chute 12 from collecting on the inverted U-shaped reinforcing ply 20 prior to passage of the ply through the limited clearance corners formed between angles 9, 10, triangular planar member 4 and vertical planar member 3. Collection of fibers on the inverted U-shaped reinforcing ply 20 could cause jamming or tearing at these points.

The reinforcing ply 20 is introduced into the fiber deposition chute 12 while in the inverted U-shaped in order to permit formation of a substantially planar lowermost layer of airfelt 21 which lies adjacent the lowermost surface of the reinforcing ply 20 in the finished absorbent pad embodiment. Internal airflow baffling techniques well known in the art may be employed within the vacuum chamber 26 to minimize any discontinuities in the cross-machine direction uniformity of the airfelt layer 21 which might otherwise occur due to the minor obstruction presented by the thin U-shaped shroud 28. In a particularly preferred embodiment, the lowermost layer of airfelt 21 is formed directly over a ply 23 of wet strength tissue paper in the forwardmost portion 13 of the fiber deposition chute 12. The ply 23 is preferably similar to that utilized as the reinforcing ply 20. As can be seen in FIG. 2, the vacuum chamber 25 located adjacent the lowermost surface of the moving foraminous support member 11 is preferably divided into two distinct segments 26, 27 by means of an adjustable dividing wall 19 which may be advanced or retarded in the machine direction as shown by arrows 201, 202. The vacuum chamber 25 is preferably segmented as outlined above in order to permit the application of differing vacuum levels between the leading portion 13 of the fiber deposition chute 12 and the trailing portion 14, since the trailing portion encounters more resistance to air flow than the leading portion due to the presence of the fibrous layer 21 and the reinforcing ply 20 during formation of the uppermost layer of airfelt 22.

As is apparent from FIGS. 1 and 2, the reinforcing ply 20 is maintained in an inverted U-configuration until the desired thickness of airfelt layer 21 has been obtained. The relative and total thickness of the respective airfelt layers 21 and 22 is controllable not only by the rate of fiber deposition within the chute 12, but also by the level of vacuum applied beneath the moving foraminous support member 11 in vacuum chamber segments 26 and 27, the machine direction positioning of the segmenting wall 19 within the vacuum chamber 25, and the machine direction positioning of the triangular planar member 4 connected to vertical planar member 3. Furthermore, baffle plates 15 and 16 which extend across the entire width of the fiber deposition chute 12, and which may be adjusted about pivot points 17 and 18, may also be employed to direct the flow of fibers issuing from fiber disintegration means 501, which are well known in the art and which are partially shown in schematic form only in FIG. 2, toward either the leading portion 13 or the trailing portion 14 of the deposition chute 12, depending upon the desired split between uppermost layer 22 and lowermost layer 21.

Angular guides 9 and 10 force the reinforcing ply 20 to remain in contact with the leading surface of triangular planar member 4 which is identical in size and shape to triangular planar member 2 as the center of reinforcing ply 20 is directed about the apex of triangular planar member 4. This in turn forces the reinforcing ply 20 to resume a planar configuration as it passes downwardly to the base portion of the trailing surface of triangular planar member 4. Direction changing roll 6 restores the reinforcing ply 20 to its original direction of travel and exposes the uppermost surface of the ply to the deposition of fibers in the downstream portion 14 of the fiber deposition chute 12. A fibrous airlaid web 22 is thus formed adjacent the uppermost surface of the reinforcing ply 20 prior to passage of the assemblage from the fiber deposition chute 12. A ply 24 of wet strength tissue paper is preferably thereafter brought into contact with the uppermost surface of the absorbent airfelt layer 22 about direction changing roller 30, as shown in FIG. 2, to form a reinforced fibrous web structure encapsulated on both sides by plies 23, 24 of wet strength tissue paper.

As has been pointed out earlier herein, the relative position of the internally located reinforcing ply 20 may be adjusted intermediate the uppermost and lowermost surfaces of the resultant absorbent pad structure by advancing or retarding the position of the folding board 1 and the direction changing rollers 5, 6, which are preferably mounted thereto, within the fiber deposition chute 12. This of course necessitates a corresponding adjustment of angular guides 7, 8, 9 and 10 and shroud 28 in order to maintain the reinforcing ply 20 in contact with each of the two surfaces of triangular planar members 2, 4 which intersect vertical planar member 3. The U-shaped shroud 28 illustrated in cross-section in FIG. 3 is preferably employed in the practice of the present invention to avoid the collection of fibers on the uppermost surfaces of the reinforcing ply 20 prior to direction of the ply intermediate angular guides 9 and 10 located at the interior corners formed between triangular planar member 4 and vertical planar member 3. This is necessary to avoid hangup or jamming of the ply within the relatively tight clearances provided intermediate the guides 9 and 10 and the interior corners formed by triangular planar member 4 and vertical planar member 3. As will thus be apparent to those skilled in the art, the shroud 28 must also be adjustable such that adjustment of triangular planar member 4 in the machine direction will not result in exposure of the inverted U-shaped reinforcing ply 20 to the stream of fibers present in the leading portion 13 of fiber deposition chute 12. In a most preferred embodiment of the present invention, separating wall 19 in vacuum chamber 25 is adjustable so as to vertically coincide with the position ultimately assumed by triangular planar member 4 within the deposition chute 12.

FIG. 4 is a simplified perspective illustration of the embodiment of the present invention illustrated in FIGS. 1–3. Selected portions of the fiber deposition chute 12 have been broken away to illustrate with maximum clarity the present pad forming operation.

Figure 6:
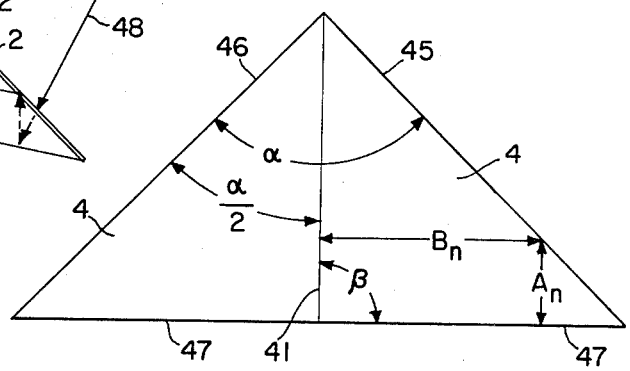
FIG. 6 is a discharge end view of the folding board illustrated in FIG. 5.
Figure 7:
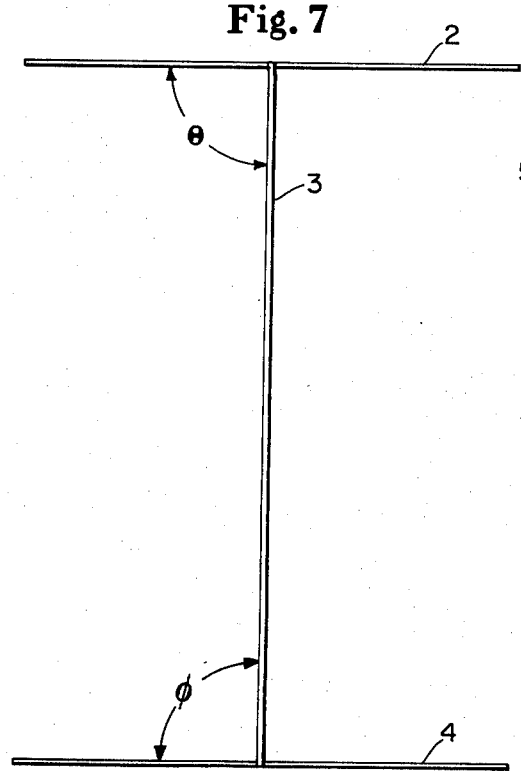
FIG. 7 is a plan view of the folding board illustrated in FIG. 5.

The geometry of the folding board 1 illustrated in FIGS. 1–4 is more clearly set forth in FIGS. 5–7. While it is not essential that the folding board 1 be comprised of solid sheet stock as illustrated in FIG. 5, the folding board preferably comprises a pair of planar members 2, 4, each in the shape of an isosceles right triangle, connected to one another by means of a vertical planar member 3 corresponding in height to the altitude of said isosceles triangles. In order to minimize the vertical height requirement for a folding board of the present invention, it is preferable that the center of the reinforcing ply 20 be made to coincide with the altitude of both triangles during its passage over the folding board. Thus, in the simple embodiment illustrated in FIG. 4 the included right angle $\alpha$ of triangular planar member 2 is surrounded by equal length legs 42, 43 while the included right angle $\alpha$ of identical triangular planar member 4 is surrounded by equal length legs 45, 46. The base 44 of the isosceles triangle embodied in planar member 2 and the base 47 of the isosceles triangle embodied in planar member 4 connect the respective equal length leg segments of the triangles. Lines 40 and 41 illustrated in FIG. 5 represent the altitudes of the right triangles embodied in planar member 2 and 4, respectively. Thus, the angle $\beta$ in each case amounts to 90 degrees, and the included right angle $\alpha$ of each triangle is bisected by its respective altitude. The angle $\gamma$ between the altitude 40 of the right triangle embodied in planar member 2 and the base of vertical planar member 3 and the angle $\delta$ between the altitude 41 of the right triangle embodied in planar member 4 and the base of vertical planar member 3 in the illustrated embodiment are also equal to 90 degrees.

The principle upon which the folding board 1 illustrated in FIGS. 1–7 operates is that each point on the incoming reinforcing ply 20 must travel the same linear distance in traversing the surface of the forming board from entry thereon near the base 44 of the isosceles right triangle embodied in planar member 2 until its exit therefrom near the base 47 of the isosceles right triangle embodied in planar member 4. The paths followed by a pair of corresponding points located on opposite sides of the reinforcing ply's center are represented by lines 48 and 49 in FIG. 5. The principle is further illustrated in FIG. 6 which is a discharge end view of the folding board 1 illustrated in FIG. 5. The sum of any given pair of lines $A_n + B_n$ must be constant, where $A_n$ is any line parallel to the altitude 41 of the triangle embodied in planar member 4 and $B_n$ is the corresponding horizontal distance of the line $A_n$ from the altitude 41.

As should be clear from FIG. 7 which is a plan view of the folding board 1 illustrated in FIG. 5, the lowermost layer of absorbent fibers 21 is formed while the reinforcing ply 20 is in the inverted U-configuration intermediate triangular planar members 2, 4. As will be appreciated by those skilled in the art, it is desirable to minimize the width occupied by the reinforcing ply 20 as it passes through the fiber deposition chute 12 in the inverted U-configuration in order to minimize any cross-machine direction non-uniformity in the lowermost layer of absorbent fibers 21 formed adjacent its lowermost surface.

While it should be observed that the angle $\theta$ formed between triangular planar member 2 and vertical planar member 3 and the angle $\phi$ formed between triangular planar member 4 and vertical planar member 3 amounts to 90 degrees in the embodiment illustrated in FIGS. 1–7, it should be noted that the angles $\theta$ and $\phi$ need not equal one another, nor is it required that either angle be a right angle. The angle of infeed and outfeed of the reinforcing ply 20 may be varied as desired, provided only that the angles employed permit the reinforcing ply to be maintained in substantial surface contact with triangular planar members 2, 4 at the inside corners formed between the triangular planar members and vertical planar member 3. It should further be noted that vertical planar member 3 is not an essential portion of the present folding board 1, but rather is employed in a preferred embodiment of the present invention as a means of securing the triangular planar members in longitudinal alignment with one another, a feature which is critical to the practice of the present invention.

It is possible to substitute other suitable means of maintaining the reinforcing ply 20 in contact with the inside corners formed between triangular planar members 2, 4 and vertical planar member 3 for the angular guides 7, 8, 9 and 10 illustrated in FIGS. 1 and 2. Thus, rods, rolls, or any other suitable mechanism may be employed, provided only that the overall distance traveled by any given point on the reinforcing ply remain substantially constant across the width of the ply. In this regard, it should be noted that sharp edges are preferably removed from portions of the folding board 1 where stress concentrations are particularly high in order to avoid cutting or tearing of the reinforcing ply by the tensional forces to which it is subjected as it is drawn through the folding board. In this regard, a slight relief is preferably provided at the leading and trailing surfaces of the triangular planar members 2, 4 at their respective apexes. While this causes a very slight deviation in the theoretical constant length criteria described above, the practical and beneficial effect is to minimize the tendency of the reinforcing ply 20 to rip or tear at points of stress concentration.

Figure 8:
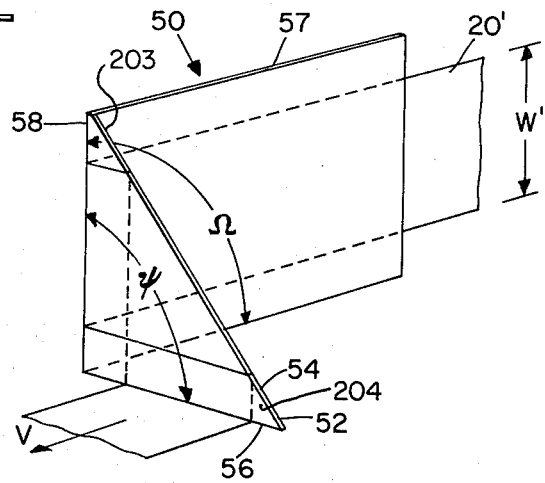
FIG. 8 is a simplified perspective view of yet another folding board suitable for use in the present invention.

FIG. 8 represents yet another particularly preferred embodiment of a folding board 50 which may be employed in the practice of the present invention in a system similar to that illustrated in FIGS. 1 and 2. In the embodiment illustrated in FIG. 8, a vertical support member 57 is joined to one of the equal length legs 58 of an isoceles right triangle embodied in planar member 52, said isosceles right triangle having its included right angle $\Psi$ located intermediate equal length legs 58, 56. The triangular planar member 52 preferably forms an angle $\Omega$ of 90 degrees with vertical planar member 57. The leading surface of triangular member 52 is designated 203 and its trailing surface 204. In practice, a reinforcing ply 20' having a width W' is fed in a vertical plane in a direction parallel to the direction of travel of the foraminous support member 11 illustrated in FIGS. 1 and 2. The incoming reinforcing ply 20' is wrapped about leg 58 of the isoceles right triangle embodied in planar member 52 such that it contacts the trailing surface of the triangular planar member and its borders parallel the equal length leg 56. The reinforcing ply 20' is thereafter wrapped over the hypotenuse 54 of the triangular planar member 52 and moves downwardly in a direction parallel to leg 58 while in contact with the leading surface 203 of the triangular planar member. The reinforcing ply 20' is finally directed beneath equal length leg 56 of triangular planar member 52 thereafter continues in a manner similar to that illustrated in FIGS. 1 and 2. The particular embodiment illustrated in FIG. 8 offers the advantage that the reinforcing ply 20' does not require the use of any external guides to hold it in intimate contact with the surfaces of triangular planar member 52, but rather is wrapped tightly thereabout by means of the tension employed to draw the ply around the folding board 50. Furthermore, there is not interruption of the fiber forming zone in the leading portion 13 of the fiber deposition chute 12, since the vertical support member 57 may be located adjacent the edge of the fibrous layer 21. Accordingly, it is feasible to obtain a uniform cross-machine direction basis weight and profile in the fibrous airfelt layer 21 formed adjacent the lowermost surface of the reinforcing ply 20'. The embodiment illustrated in FIG. 8 does, however, require greater overhead clearance at the fiber deposition chute 12 due to the fact that the reinforcing ply 20' is not folded upon itself, as in the case of the embodiment illustrated in FIGS. 1–3.

In a particularly preferred embodiment of the present invention, the outermost plies 23, 24 of wet strength tissue paper illustrated in FIGS. 1 and 2 may be somewhat wider than the reinforcing ply 20 and the airfelt layers 21 and 22. In such an embodiment the lateral edge portions of plies 23 and 24 may be secured to one another by folding, by adhesives, or by other means well known in the art to form a continuous encapsulating envelope. If desired, a continuous layer of moisture-pervious topsheet material 101 may be fed by means well known in the art, i.e., as by roll 130, into contact with the uppermost surface of tissue ply 24 and thereafter secured in superposed relation to the continuous envelope. Absorbent pad segments 103 of predetermined length are thereafter cut from the continuous envelope. As shown in the downstream segments of FIGS. 1 and 2, the absorbent pad segments are preferably rotated 90° prior to securement to a continuous web of moisture-impervious backsheet material 102 about their periphery to form a continuous web of disposable absorbent bandages, such as diapers. Individual diapers are thereafter cut from the continuous web intermediate the absorbent pad segments. U.S. Pat. No. 3,952,745 issued to Duncan on Apr. 27, 1976 and incorporated herein by reference is generally representative of such a construction. Aligning the machine direction of the tissue plies 20, 23 and 24 parallel to the waistband portions of the diaper in this manner is generally desirable since it aligns the tissue's direction of maximum strength with the direction in which the greatest tensile loads are typically applied in-use.

It is noteworthy that the invention disclosed herein may be utilized to provide plies which are perforate or imperforate and which are either continuous or discontinuous in the cross-machine direction intermediate a pair of fibrous layers in a single fiber deposition zone. Furthermore, multiple plies may be simultaneously fed utilizing an embodiment of the present invention, or multiple stages of the present invention may be employed to provide multiple reinforcing plies within a single structure, each ply being separated from the next by a fibrous layer. In addition, it should be noted that although in the embodiment illustrated in FIGS. 1–3 it is preferable to align the center of the reinforcing ply 20 with the altitude of the right triangles embodied in planar members 2, 4 to minimize overall height requirements in the deposition chute 12, the lateral positioning of the reinforcing ply 20 may be altered as desired relative to the apex of the triangular planar members and will maintain the selected position until manually repositioned. This is due to the fact that the laterally imposed forces introduced on the ply by the illustrated system remain in total balance with one another as the ply is tracked through the folding board. Thus, there is nothing to disturb the equilibrium established once the desired position of the reinforcing ply relative to the apex of the triangular planar member or members has been established.

While the present invention has been described in particular detail with reference to several preferred embodiments, it is not intended to hereby limit to the particular embodiments shown and described. Many other variations of the present invention will be apparent to those skilled in the art.

What is claimed is:

1. An in-line fiber deposition apparatus for continuously vacuum forming an airlaid fibrous fluff web adjacent the uppermost and lowermost surfaces of a substantially planar reinforcing ply having substantially the same width as said web, said apparatus comprising:
    (a) fiber disintegration means;
    (b) a continuous fiber deposition chamber interconnected to said fiber disintegration means;
    (c) a continuously moving foraminous support member passing through said deposition chamber in a plane substantially perpendicular to the direction of fiber flow;
    (d) suction means located adjacent the surface of said foraminous support member opposite said fiber disintegration means;
    (e) means for introducing said reinforcing ply to said deposition chamber in a first direction identical to that of said foraminous support member while said ply is oriented in a first plane such that its width is substantially parallel to the direction of fiber flow within said chamber to facilitate vacuum forming the portion of said airlaid fibrous fluff web adjacent the lowermost surface of said reinforcing ply on said foraminous support member;

(f) guide means extending perpendicular to said first direction of travel within said fiber deposition chamber for abruptly reorienting said reinforcing ply to a second plane perpendicular to said first plane while restoring said ply to said first direction of travel to facilitate vacuum forming the portion of said airlaid fibrous fluff web adjacent the uppermost surface of said reinforcing ply; and (g) means for removing said ply and said airlaid web portions from said fiber deposition chamber.

2. The apparatus of claim 1, wherein said guide means for abruptly reorienting said reinforcing ply is comprised of a planar member exhibiting the shape of an isosceles right triangle having one of its equal length leg portions oriented perpendicular to said first direction of travel of said reinforcing ply and the other of its equal length leg portions in a second plane perpendicular to said first plane, said second plane being parallel to the plane of said foraminous support member.

3. The apparatus of claim 1, wherein the position of said guide means for abruptly reorienting said reinforcing ply is adjustable in the machine direction within the fiber deposition chamber to vary the relative thickness of the uppermost and lowermost airfelt web portions.

4. The apparatus of claim 1, wherein the suction means located adjacent the surface of said foraminous support member is comprised of a vacuum chamber having a length at least equal to that of said fiber deposition chamber, said vacuum chamber having an internal partition member oriented perpendicular to the direction of travel of said ply, said partition member being adjustable in the machine direction to facilitate alignment thereof with said guide means for abruptly reorienting said reinforcing ply within said chamber and thereby facilitate the application of a higher level of suction during formation of the airlaid fibrous fluff web portion adjacent the uppermost surface of said reinforcing ply.

5. The apparatus of claim 1, including means for feeding a first tissue ply having a width at least as great as said reinforcing ply into superposed relation with said foraminous support member prior to entry thereof into said fiber deposition chamber and means for feeding a second tissue ply having a width at least as great as said reinforcing ply into superposed relation with the uppermost surface of said uppermost airlaid fibrous fluff web portion upon exit thereof from said fiber deposition chamber.

6. An in-line fiber deposition apparatus for continuously vacuum forming an airlaid fibrous fluff web adjacent the uppermost and lowermost surfaces of a substantially planar reinforcing ply having substantially the same width as said web, said apparatus comprising:

(a) fiber disintegration means;

(b) a continuous fiber deposition chamber interconnected to said fiber disintegration means;

(c) a continuously moving foraminous support member passing through said deposition chamber in a plane substantially perpendicular to the direction of fiber flow;

(d) suction means located adjacent the surface of said foraminous support member opposite said fiber disintegration means;

(e) means for continuously feeding said reinforcing ply in the same direction as said foraminous support member while oriented in a first plane parallel to that of said foraminous support member;

(f) first guide means extending in a direction perpendicular to said direction of travel for abruptly causing said reinforcing ply to invert and fold about itself in a second plane perpendicular to said first plane;

(g) means for introducing said reinforcing ply to said fiber deposition while in a folded configuration to facilitate vacuum forming the airlaid fibrous fluff web portion adjacent the lowermost surface of said reinforcing ply;

(h) second guide means extending perpendicular to the direction of travel of said reinforcing ply within said fiber deposition chamber for abruptly reorienting said ply from a folded configuration to a planar configuration in said first plane while restoring said ply to said first direction of travel to facilitate vacuum forming the portion of said airlaid fibrous fluff web adjacent the uppermost surface of said reinforcing ply; and (i) means for removing said ply and said airlaid web portions from said fiber deposition chamber.

7. The apparatus of claim 6, wherein said first and second guide means are comprised of identical planar members exhibiting the shape of isosceles triangles located in parallel planes and secured in longitudinal alignment with one another, said triangular planar members having an included angle of approximately 90 degrees located at their apexes.

8. The apparatus of claim 7, wherein said identical planar members exhibiting the shape of isosceles triangles are secured to one another by a planar member connecting their respective altitudes.

9. The apparatus of claim 8, wherein said identical planar members exhibiting the shape of planar isosceles triangles and said connecting planar member are adjustable as a unit in the machine direction to vary the relative thickness of the uppermost and lowermost airlaid fibrous fluff web portions located on opposite surfaces of said reinforcing ply.

* * * * *

UNITED STATES PATENT AND TRADEMARK OFFICE
CERTIFICATE OF CORRECTION

PATENT NO. : 4,217,078
DATED : August 12, 1980
INVENTOR(S) : Kenneth B. Buell

It is certified that error appears in the above-identified patent and that said Letters Patent are hereby corrected as shown below:

Column 2, line 22, "isoceles" should read -- isosceles --.

Column 3, line 38, "isoceles" should read -- isosceles --.

Column 3, line 57, "U-shaped" should read -- U-shape --.

Column 7, line 18, "isoceles" should read -- isosceles --.

Column 7, line 27, after "52" insert -- and --.

Signed and Sealed this

Eleventh Day of November 1980

[SEAL]

Attest:

Attesting Officer

SIDNEY A. DIAMOND

Commissioner of Patents and Trademarks